United States Patent
Tanaka et al.

(10) Patent No.: US 7,194,890 B2
(45) Date of Patent: Mar. 27, 2007

(54) GAS CHROMATOGRAPH AND EXPIRED AIR COMPONENT ANALYZER

(75) Inventors: Katsuyuki Tanaka, Suita (JP); Mariko Sugimura, Himeji (JP); Junko Yanagitani, Itami (JP); Noriko Kiyoshi, Kobe (JP); Kazuo Onaga, Osaka (JP); Hiroshi Koda, Sanda (JP)

(73) Assignees: FIS Inc. (JP); Abilit Corporation (JP)

( * ) Notice: Subject to any disclaimer, the term of this patent is extended or adjusted under 35 U.S.C. 154(b) by 32 days.

(21) Appl. No.: 10/506,421

(22) PCT Filed: Feb. 20, 2003

(86) PCT No.: PCT/JP03/01891

§ 371 (c)(1),
(2), (4) Date: Mar. 11, 2005

(87) PCT Pub. No.: WO03/075001

PCT Pub. Date: Sep. 12, 2003

(65) Prior Publication Data

US 2005/0160790 A1    Jul. 28, 2005

(30) Foreign Application Priority Data

Mar. 4, 2002   (JP) ............................ 2002-057885

(51) Int. Cl.
*B01D 15/08*   (2006.01)
(52) U.S. Cl. .................... 73/23.42; 73/23.24
(58) Field of Classification Search ........... 73/23.24, 73/23.42
See application file for complete search history.

(56) References Cited

U.S. PATENT DOCUMENTS 3,366,149 A * 1/1968 Taft et al. ............... 141/82
3,430,418 A * 3/1969 Wagner .................. 95/100

(Continued)

FOREIGN PATENT DOCUMENTS

| JP | 56-028304 A1 | 8/1981 |
| JP | 58-112960 A1 | 8/1983 |
| JP | 10-019865 A1 | 1/1998 |

OTHER PUBLICATIONS

Skoog, Douglas A. Principles of Instrumental Analysis, Saunders College Publishing, 3rd ed., 1984, p. 751-53.*

(Continued)

*Primary Examiner*—Michael Cygan
(74) *Attorney, Agent, or Firm*—Rader, Fishman & Grauer PLLC (57) ABSTRACT

A gas chromatograph having the capability of performing a reliable measurement under a condition that the baseline of a detector output is stabilized, and a breath component analyzer using the same are provided. This gas chromatograph comprises a gas separation column accommodating a member for causing a flow delay depending on gas component; air pump for supplying an air as a carrier gas into the gas separation column; gas supply port formed in a gas flow channel extending between the air pump and the gas separation column, and adapted to supply a subject gas containing a target gas component to be detected into the carrier gas flowing in the gas flow channel; buffer tank provided upstream of the gas supply port; and a detector for detecting the gas component of the subject gas supplied into the gas separation column.

12 Claims, 8 Drawing Sheets

U.S. PATENT DOCUMENTS 3,455,817 A * 7/1969 Modell ..................... 210/640
3,624,986 A * 12/1971 Shoemake ..................... 96/4
4,230,464 A * 10/1980 Bonmati et al. ............... 95/22
4,238,204 A * 12/1980 Perry ........................... 95/55
4,994,096 A * 2/1991 Klein et al. .................... 95/15
6,074,461 A * 6/2000 Wilson ....................... 96/102
6,293,995 B2 * 9/2001 Wilson ......................... 95/23

OTHER PUBLICATIONS

International Search Report for PCT/JP03/01891 mailed on Apr. 22, 2003.

* cited by examiner

| Gas Species | Change in Output of Detector (mV) | Gas Concentration of Breath Odor Component | |
|---|---|---|---|
| | | ppb unit | ng/l unit |
| $H_2S$ | 101 | 884 ppb | 1345 ng/l |
| $CH_3SH$ | 42.5 | 381 ppb | 818 ng/l |
| $(CH_3)_2S$ | nd | nd ppb | nd ng/l |

# GAS CHROMATOGRAPH AND EXPIRED AIR COMPONENT ANALYZER

TECHNICAL FIELD

The present invention relates to a gas chromatograph, which is widely available for qualitative/quantitative analysis of a component in a subject gas, and a breath component analyzer using the same.

BACKGROUND ART

A gas chromatograph provides a gas chromatogram, which is prepared by introducing a subject gas to be detected together with a carrier gas into a gas separation column having a filling material therein, separating a gas component from the subject gas according to a deference in retention time caused by the interaction between the subject gas and the filling material in the gas separation column, and then detecting the separated gas component by a detector such as thermal conductivity detector (TCD) or flame ionization detector (FID).

At this time, since the retention time of the gas component in the gas separation column depends on temperature, the gas separation column is placed in a thermostatic chamber, and kept at an elevated temperature, so that the retention time of the gas component in the gas separation column can be maintained constant. As a result, accurate measurement becomes possible.

Figure 14:
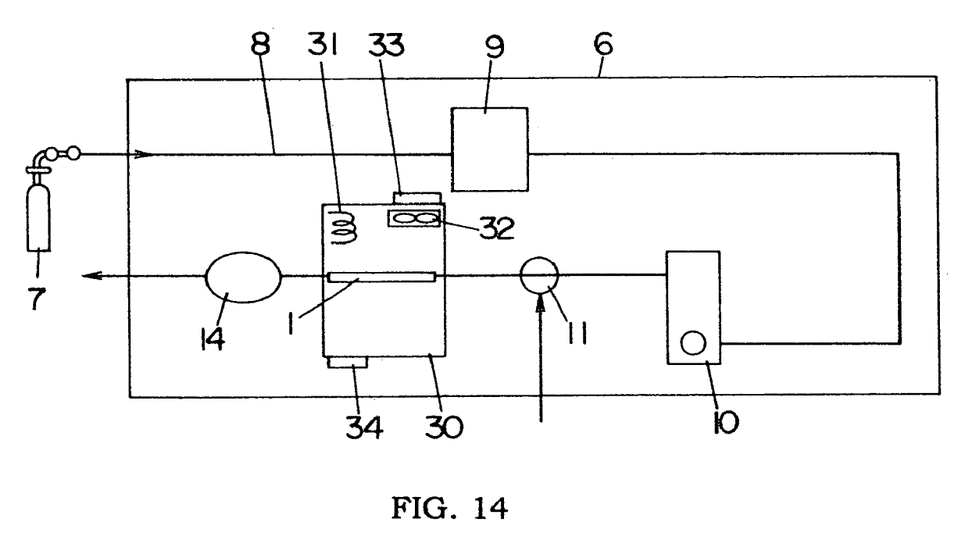
FIG. 14 is a schematic diagram illustrating a flow channel configuration of a conventional gas chromatograph using a gas cylinder.

FIG. 14 is a schematic diagram showing this kind of gas chromatograph 6. A flow amount of a carrier gas supplied from a gas cylinder 7 through a gas flow channel 8 is controlled by a flow regulator 9. After the flow amount is detected by a flow sensor 10, a subject gas to be measured is supplied from a gas injection port 11, so that a mixture gas of the carrier gas and the subject gas is introduced into a gas separation column 1. The gas separation column 1 is placed in a thermostatic chamber 30, and kept constant at an elevated temperature. The gas provided from the gas separation column 1 is detected by a detector 14 to obtain the chromatogram.

The thermoplastic chamber 30 is composed of a heater 31, fan 32, and suction and discharge ports 33, 34, which have adjustable apertures. In the case of heating the gas separation column 1, the heater 31 is activated, and the fan 32 is rotated to send the air heated by the heater 31 to the gas separation column 1. The temperature of the gas separation column 1 is controlled by adjusting the apertures of the suction and discharge ports 33, 34 or a supply amount of electric power to the heater 31. In addition, when cooling the gas separation column 1, the suction and discharge ports 33, 34 are fully opened, and the fan 32 is rotated to circulate outside air through the thermostatic chamber 30.

By the way, in the gas chromatograph described above, the thermostatic chamber 30 must have a sufficient volume to stably keep the gas separation column 1 at the elevated temperature. Due to this reason, the device is easily large-sized as a whole. Particularly, in the medical field, it is being considered to introduce the gas chromatograph for a breath component analyzer for early detection of disease and monitoring of medical treatment effects, and the development of small-sized gas chromatograph is being expected.

In addition, according to the above device configuration, a pressurized carrier gas is sent from the gas cylinder 7 to the gas separation column 1. To downsize the device, it is suggested to use air as the carrier gas in place of the gas cylinder. However, there is a problem that the baseline of output of the detector 14 fluctuates due to the influence of miscellaneous gas mixed in the air, so that qualitative/quantitative analysis can not be achieved with reliability.

SUMMARY OF THE INVENTION

In view of the above-mentioned problems, a concern of the present invention is to provide a gas chromatograph having advantages that downsizing is possible, and a reliable analysis can be achieved by stabilizing the baseline of output of a detector even when using air as a carrier gas.

That is, the gas chromatograph device of the present invention comprises a gas separation column accommodating a member for causing a flow delay depending on gas component; an air pump for supplying an air as a carrier gas into the gas separation column; a gas supply port formed in a gas flow channel extending between the air pump and the gas separation column, and adapted to supply a subject gas containing a target gas component to be detected into the carrier gas flowing in the gas flow channel; a buffer tank provided upstream of the gas supply port, and having the capability of retaining a larger amount of the carrier gas than the amount of the carrier gas supplied per unit of time into the gas separation column by the air pump; and a detector for detecting the gas component of the subject gas supplied to the gas separation column.

According to the present invention, even when a miscellaneous gas component is included in the carrier gas of the air supplied from the air pump, the carrier gas is sent to the gas separation column through the buffer tank for weakening the flow of the air and making concentration uniform. Therefore, it is possible to prevent the baseline fluctuation of output of the detector, and provide the reliable analysis.

A further concern of the present invention is to provide a gas chromatograph having advantages that downsizing is possible, and a reliable analysis can be achieved by stabilizing the baseline of output of a detector with use of a bag-type tank having a variable volume, in which the carrier gas such as a clean air is filled, in place of a gas cylinder.

That is, this gas chromatograph comprises a gas separation column accommodating a member for causing a flow delay depending on gas component; a bag-type tank, which is of a variable volume to retain the carrier gas therein, and has a connection port connected to an end of the gas separation column through a gas flow channel; an air suction pump provided at the other end of the gas separation column; a gas supply port formed between the gas separation column and the bag-type tank to supply a subject gas including a target gas component to be detected into the carrier gas flowing in the gas flow channel; and a detector for detecting the gas component of the subject gas supplied to the gas separation column.

Since only the clean air including no miscellaneous gas component filled as the carrier gas in the bag-type tank is sent to the gas separation column, it is possible to carry out the reliable analysis, while preventing the baseline fluctuation of output of the detector caused by the influence of the miscellaneous gas component. In addition, the device can be easily downsized, as compared with the case of using the gas cylinder.

It is preferred that the gas chromatograph further comprises a sensor for sensing a timing of injecting the subject gas into the gas flow channel, and an analysis unit for analyzing the subject gas according to the timing provided from the sensor and an output of the detector.

In the above gas chromatograph, it is preferred that the buffer tank has an end opened to outside, and the other end connected to the air pump, and a part of the carrier gas supplied to the gas flow channel by the air pump is sent to the gas separation column, and the rest of the carrier gas is returned from the gas flow channel to the buffer tank through a branch channel. In this case, it becomes possible to use a low-cost multipurpose air pump having the capability of providing a larger suction amount than the flow amount of the carrier gas supplied to the gas separation column.

It is also preferred that the above gas chromatograph further comprises a gas purifier using at least one of a gas decomposition catalyst and a gas absorption material, which is disposed upstream of the gas supply port in the gas flow channel. In this case, even when a high concentration of a miscellaneous gas is included in the carrier gas, or the miscellaneous gas exists in the carrier gas for an extended time period, it is possible to surely remove the miscellaneous gas remaining in the carrier gas.

Moreover, it is preferred that the gas chromatograph further comprises a flow sensor disposed upstream of the gas supply port and at the vicinity of the gas supply port in the gas flow channel, or downstream of the detector and at the vicinity of the detector in the gas flow channel, and means of detecting a supply of the subject gas according to a change in output of the flow sensor. In this case, it is possible to accurately detect the timing of gas injection as the measurement standard of retention time, and consequently further improve the analysis accuracy of the gas component.

In addition, it is preferred that the gas chromatograph further comprises a controller for increasing a flow amount of the carrier gas supplied into the gas separation column according to a predetermined pattern from the time point of supplying the subject gas. In this case, even when the gas component is of a slow (long) retention time, it is possible to improve gas separation performance, and therefore reduce analysis time. Furthermore, since a peak indicating a detection of the gas component by the detector has a sharp rising edge, conversion of concentration can be achieved more accurately.

Another concern of the present invention is to provide a breath component analyzer having the capability of carrying out a componential analysis of breath gas by use of the above-described gas chromatograph. This breath component analyzer comprises a memory for storing reference data including a retention time previously determined by the gas chromatograph with respect to a breath odor sample having a known gas component; and an analysis unit for comparing measurement data including a retention time determined by the gas chromatograph with respect to a breath odor to be measured with the reference data.

It is preferred that the breath component analyzer further comprises a unit of correcting a fluctuation amount of the retention time of the gas component corresponding to the breath odor to be detected according to the fluctuation amount of the retention time of a constant component in breath. In this case, even when a flow fluctuation of the carrier gas occurs, it is possible to appropriately correct the retention time of the gas component in the expired gas, and prevent deterioration of analysis accuracy of the gas component.

These and still other objects and advantages of the present invention will become more apparent from the detail description of the invention and embodiments described below.

BEST MODE FOR CARRYING OUT THE INVENTION

The present invention is explained in detail below according to preferred embodiments.

First Embodiment

Figure 1:
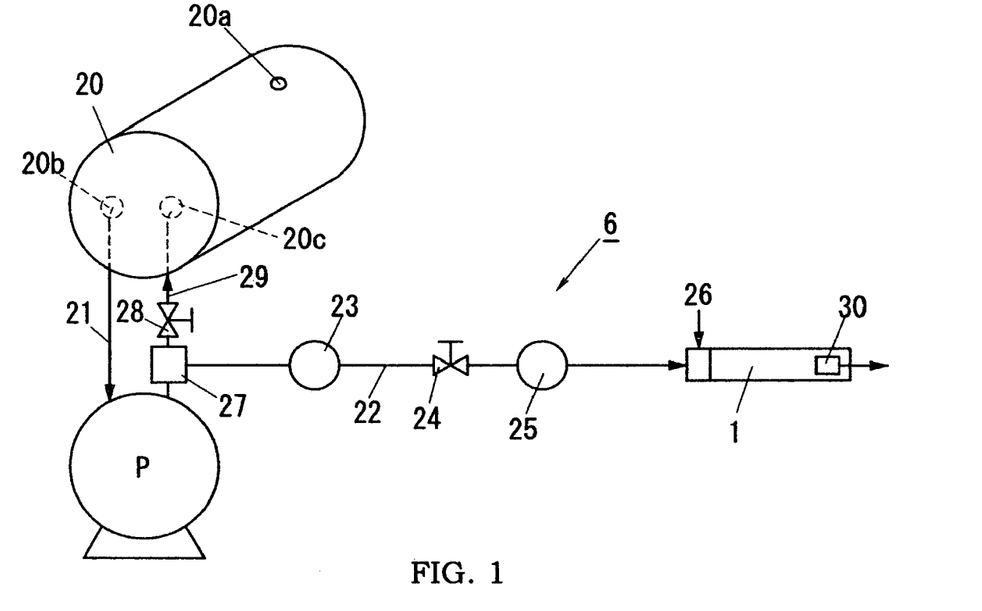
FIG. 1 is a schematic diagram illustrating a flow channel configuration of a gas chromatograph according to a first embodiment of the present invention.

FIG. 1 is a schematic diagram illustrating a flow channel configuration of a gas chromatograph 6 of the present embodiment. This gas chromatograph 6 is mainly composed of a gas separation column 1 accommodating a member of causing a flow delay depending on gas component, air pump P for pressure feeding an air as a carrier gas to the gas separation column 1, gas supply port (hereinafter referred to as a gas injection port) 26 formed in a gas flow channel 22 extending between the air pump P and the gas separation column 1 to supply a subject gas including a target gas component to be detected into the carrier gas flowing in the gas flow channel 22, buffer tank 20 disposed upstream of the air pump, and a detector 30 for detecting the gas component of the subject gas supplied into the gas separation column 1.

The buffer tank 20 is formed in a bottle shape having a suction port 20a of a small aperture communicated with outside, discharge port 20b, and a return port 20c. The air pump P is connected to the discharge port 20b of the buffer tank 20 through a gas intake channel 21. The air sucked and pressurized by the air pump P through the buffer tank 20 is sent as the carrier gas to the gas separation column 1 through the gas flow channel 22.

In FIG. 1, the numeral "23" designates a gas purifier disposed in the gas flow channel 22. The numeral "24" designates a flow regulator comprising a needle valve. The numeral "25" designates a flow sensor for detecting a change in pressure in the gas flow channel 22. In addition, the numeral "27" designates a branch portion formed in the gas flow channel 22 between the air pump P and the gas purifier 23. The numeral "28" designates a speed controller for controlling a flow velocity of the carrier gas returned from the branch portion 27 to the buffer tank 20. The numeral "29" designates a gas return channel extending from the branch portion to the return port 20c of the buffer tank 20 through the speed controller 28. The detector 30 comprising a semiconductor gas sensor is disposed in the vicinity of an exhaust port communicated with the air in the gas separation column 1.

The buffer tank 20 has the capability of retaining a sufficiently larger amount of the carrier gas, as compared with the amount of the carrier gas supplied per unit of time into the gas separation column 1 by the air pump P. For example, in the present embodiment, since the amount of the carrier gas flowing in the gas separation column 1 is approximately 10 cc/min, the buffer tank 20 having a volume of about 1000 cc is used. As a result, a flow of the air sucked from the outside is weakened to make its concentration uniform, and then sent to the gas separation column 1. Therefore, it is possible to prevent baseline fluctuation of output of the detector 30.

When the air contains a high concentration of a miscellaneous gas, or the miscellaneous gas exists over an extended time period, the gas purifier 23 is effective to remove the miscellaneous gas. As the gas purifier 23, it is preferred to use one of a gas absorption material such as activated carbon or silica gel and a gas decomposition catalyst such as oxidation catalyst, or both of them. As the gas decomposition catalyst, it is particularly preferred to use a combustion catalyst (heated at 150° C. to 200° C. by a heater) carrying a precious metal catalyst such as platinum or platinum/palladium. The catalyst structure is not specifically restricted. For example, a honeycomb structure or a granular structure can be used.

In the case of using the gas absorption material by itself, it is not limited to the position shown in FIG. 1. For example, the gas purifier may be disposed between the buffer tank 20 and the air pump P, or upstream of the buffer tank 20. In the case of using the gas decomposition catalyst (combustion catalyst) by itself, or in combination with the gas absorption material, it is preferred to dispose the gas purifier at a region having a small flow amount of the carrier gas between the buffer tank 20 and the air pump P, or downstream of the gas supply port 26. Of course, the gas purifier 23 may be disposed at plural locations.

Figure 2:
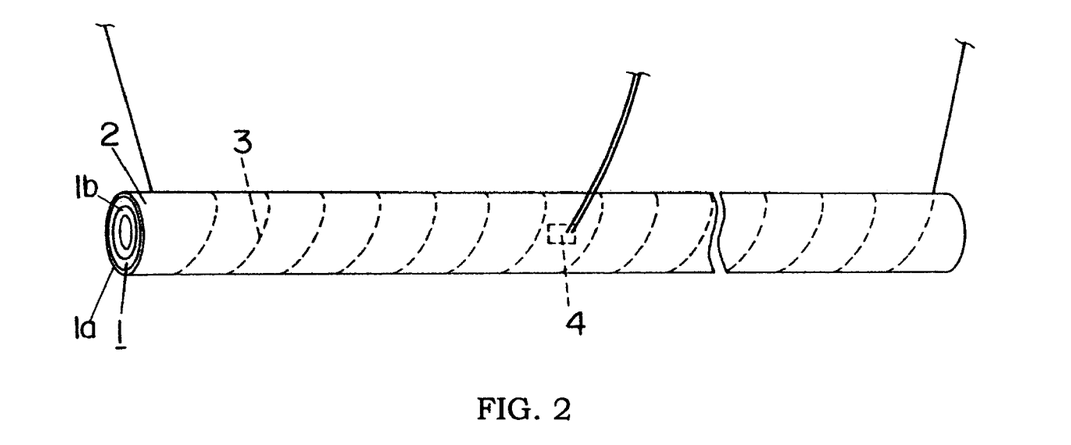
FIG. 2 is a schematic perspective view of a gas separation column of the gas chromatograph.

As the gas separation column 1, for example, it is preferred to use a structure shown in FIG. 2. This gas separation column 1 is provided by a double cylinder composed of an external cylinder 1a made of a metal having high thermal conductivity such as stainless steel or copper, and an internal cylinder 1b made of, for example, Teflon®, which is inserted in the external cylinder 1a. In the internal cylinder 1b, a filling material is filled as a stationary phase. This filling material can be appropriately selected depending on the kind of the subject gas or the carrier gas.

A heater 2 used for the gas separation column 1 comprises a flexible rubber-like heater formed by insulating a resistive element 3 with an insulation rubber such as a silicone rubber sheet. The resistive element 3 is wound in a spiral manner around the outer peripheral surface of the gas separation column 1 from its one end toward the opposite end. In addition, this gas separation column 1 has a temperature sensor 4 comprising a thermocouple to detect the temperature of the gas separation column 1. The thermocouple is coated with an insulating material such as a polyfluoroethylene resin (e.g., Teflon®) or glass wool, and then attached to the outer surface of the gas separation column 1.

At the time of operation, electricity is supplied to the heater 2 by a column heater controller described later such that the gas separation column 1 is heated at a required temperature. The column heater controller controls the amount of electricity supplied to the heater 2 according to the output of the temperature sensor 4, and if necessary, activates a cooling fan disposed in the vicinity of the gas separation column 1 to keep the gas separation column 1 at the required temperature. Thus, accurate measurement can be achieved by keeping constant the retention time of the gas component in the gas separation column 1.

Figure 3:
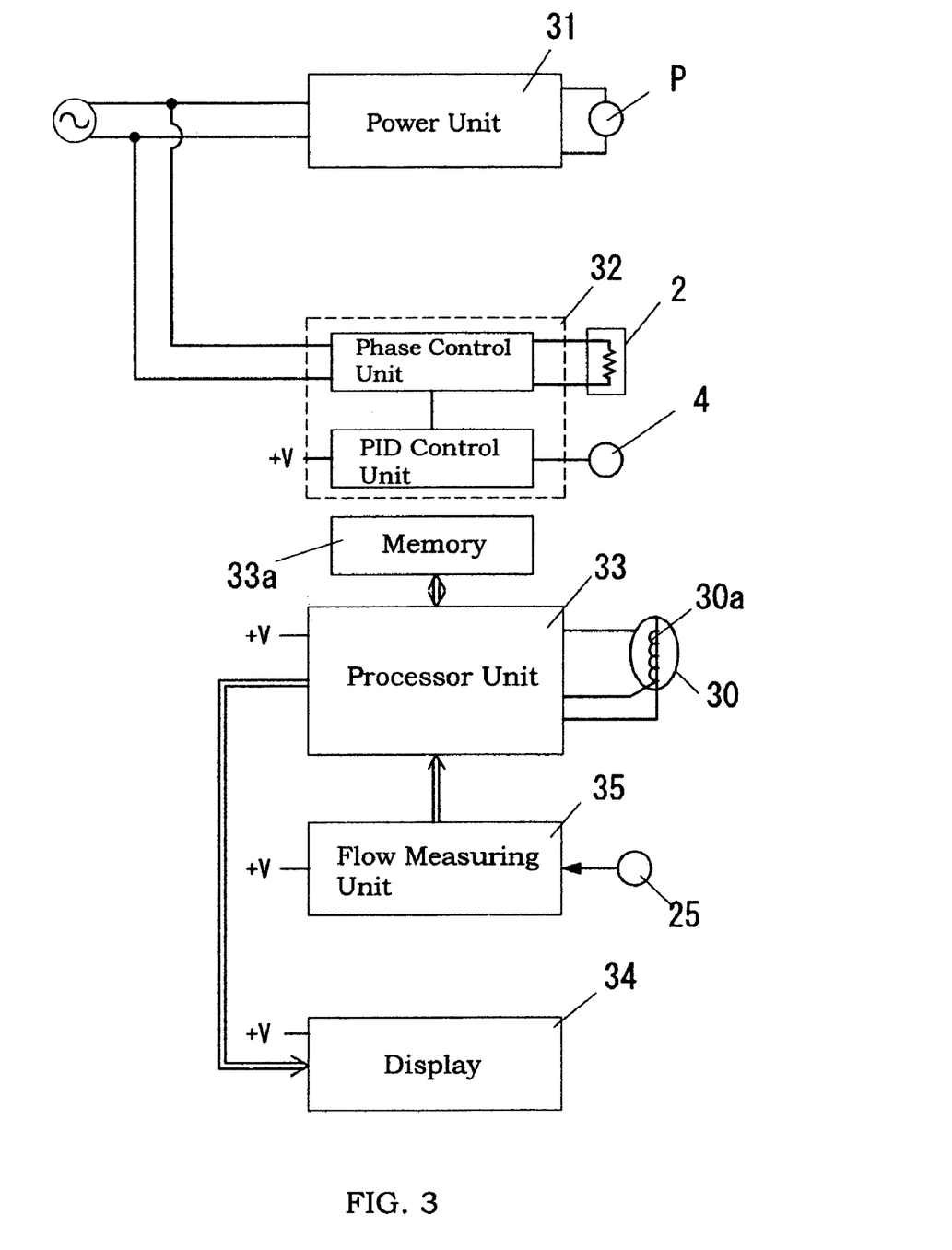
FIG. 3 is a circuit diagram of the gas chromatograph.

As shown in FIG. 3, the gas chromatograph 6 comprises a power unit 31, column heater controller 32, processor unit 33, display 34, and a flow measuring unit 35. When a power switch is turned on, the power unit 31 generates a drive voltage for the air pump P from an AC power supply, and an operation voltage +V for each of the processor unit 33, display 34, and the flow measuring unit 35.

The column heater controller 32 has a function of keeping the temperature of the gas separation column 1 at a predetermined temperature. That is, a PID control unit of the column heater controller 32 controls an electric power supplied to the heater 2 through a phase control unit according to the temperature of the heater 2 of the gas separation column 1 measured by the temperature sensor comprising a thermistor.

The processor unit 33 has a decision function of detecting the timing of injecting the subject gas from the gas injection port 26. The output of the flow sensor 25 is provided from the flow measuring unit 35, so that a change in flow amount is detected according to this sensor output. By the detection of the change in flow amount, the injection timing of the subject gas from the gas injection port 26 is determined. In addition, the processor unit 33 has an operation function for calculating the flow amount of the carrier gas in the gas flow channel 22 from the output of the flow sensor 25. Moreover, the processor unit 33 controls a supply of electricity to a heater 30a of the detector 30 comprising a gas sensor, and has a function of controlling the temperature of the detector 30 between a high-temperature period of performing a heat cleaning to a gas sensitive element of the detector 30 and a low-temperature period of receiving the sensed output of the gas sensitive element. Furthermore, the processor unit 33 has an analyzing function of analyzing the detected gas component and performing quantitative determination thereof according to the sensed output obtained during the low-temperature period and the detection of the injection timing, function of determining the temperature of the gas separation column 1 from the detection signal of the temperature sensor, and a function of sending data to the display 34.

The display 34 comprises a liquid crystal display panel and a controller, and indicates the data provided from the processor unit 33, for example, the flow amount of the carrier gas, analysis results including quantitative values of the detected gas component determined by the analyzing function, and the temperature of the gas separation column 1.

The flow sensor 25 comprises an air velocity sensor having a NTC (Negative Temperature Coefficient) thermistor and a platinum coil. This flow sensor 25 is disposed in the gas flow channel 22, and heated by applying a voltage to the platinum coil, so that the interior temperature of the heated gas flow channel 22 is sensed by the NTC thermistor.

When the carrier gas flows at a constant flow amount in the gas flow channel 22, the temperature sensed by the NTC thermistor is kept constant. However, when a change of the flow amount, i.e., a change in flow velocity occurs, the sensed temperature changes. Subsequently, when the flow amount becomes stable again, a constant temperature corresponding to the flow amount (flow velocity) is maintained. The sensed output is A/D converted by the flow measuring unit 35, and then sent to the processor unit 33. The processor unit 33 monitors the flow amount of the carrier gas by converting the sensed temperature into the flow amount.

When the power switch is turned on to drive the gas chromatograph 6, the air is sucked from outside through the buffer tank 20 by the air pump P, and a required amount of the sucked air is sent as the carrier gas to the gas flow channel 22 through the branch portion 27. The supply amount of the carrier gas to the gas flow channel 22 is controlled by the flow regulator 24. The remaining carrier gas is returned to the buffer tank 20 through the speed controller 28 and the return gas channel 29.

By allowing the carrier gas supplied into the gas flow channel 22 to pass the gas purifier 23, the miscellaneous gas component is removed. Therefore, it is possible to always send a clean carrier gas to the gas separation column 1 through the flow regulator 24. The flow amount of the carrier gas is always detected by the flow sensor 25. The processor unit 33 converts the output of the flow sensor 25 into the flow amount of the carrier gas, and monitors it. The conversion results are indicated on the display 34.

Thus, when a subject gas including a target gas component to be detected is injected in the gas injection port 26 under a condition that the carrier gas is being supplied to the gas separation column 1, the flow velocity (flow amount) in the gas flow channel 22 instantaneously decreases. In response to this momentary decrease in the flow amount, the sensed temperature of the NTC thermistor of the flow sensor 25 rises instantaneously. This momentary change in the sensed temperature is detected by the processor unit 33 from the comparison between the level of the output A of the flow sensor 25 shown in FIG. 4 and a predetermined reference level L.

Figure 4:
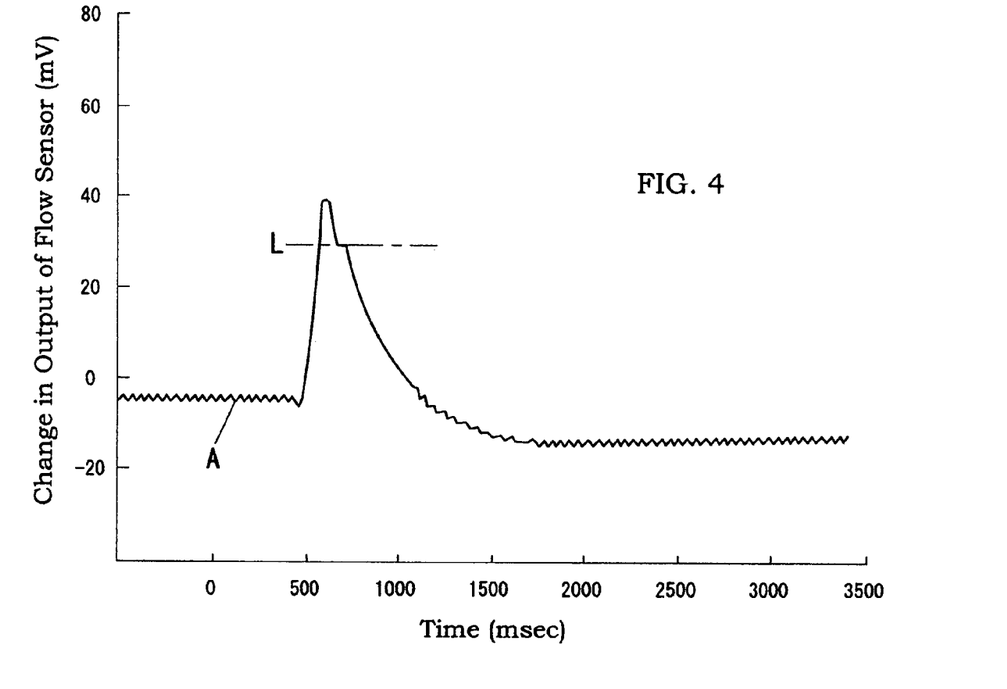
FIG. 4 is a graph explaining a detection of injection of a subject gas by the gas chromatograph.

That is, the processor unit 33 decides that the subject gas was injected at the sensed timing, and measures the retention time of the gas component to be detected by the detector 30 based on this timing. That is, in the past, a worker has operated a manual switch to detect the timing of injecting the subject gas. However, according to the gas chromatograph 6 of the present invention, the timing can be automatically detected with accuracy.

The subject gas supplied from the gas injection port 26 is mixed with the carrier gas, and a resultant mixture gas is introduced into the gas separation column 1. By allowing the mixture gas to pass the stationary phase in the gas separation column 1, the target gas component can be separated by an interaction with the stationary phase. The gas component separated by the gas separation column 1 is detected by the detector 30.

Thus, since the gas separation column 1 used in this embodiment is kept at an elevated temperature by the heater 2, it is not needed to utilize a large-scaled thermostatic chamber as in conventional devices. Therefore, by miniaturizing the heater for keeping the gas separation column 1 constant at the elevated temperature, it is possible to downsize the device as whole.

The following is an explanation about the case of using the gas chromatograph 6 described above as a breath component analyzer. This breath component analyzer has means of registering a retention time of a known gas component corresponding to a breath odor, peak of the detected output by the detector, and concentration data of the respective gas component corresponding to the peak of the detected output, and performing quantitative/qualitative analysis of the breath-odor gas component by comparing the detector output obtained with respect to the gas component corresponding to the breath odor of the subject gas with the registered data.

Gas species to be detected in a breath gas as the subject gas are already known (for example, $H_2S$, $CH_3SH$, or $(CH_3)_2S$ is selected for diabetes, liver ailment, or the period of dosing a curative medicine for alcoholic poisoning). Therefore, calibration-line data (Refer to FIG. 5) indicative of the relationship between the change in output of the detector 30 with respect to the target gas component to be detected and the gas concentration, and normalized-curve data (Refer to FIG. 6) that is peak-shape data obtained when a detected signal at the peak is defined as "1" with respect to waveform of the detected signal by the detector 30 are previously registered in the memory 33a of the processor unit 33.

Figure 5:
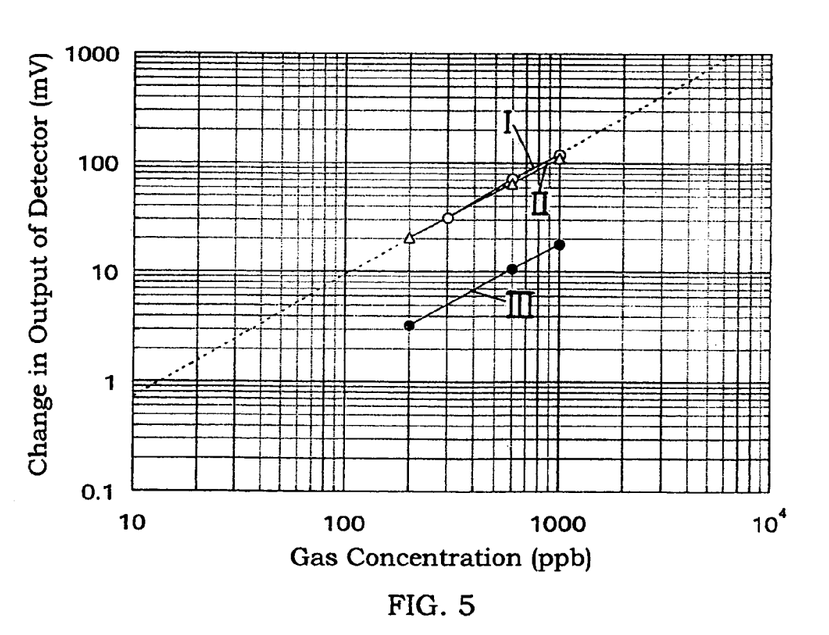
FIG. 5 shows a calibration curve registered in a processor unit of the gas chromatograph.

In FIG. 5, the horizontal axis is gas concentration (ppb), and the vertical axis is change (mV) in output of the detector 30. The calibration line is represented by $Y=aX^b$. In addition, the line "I" means that the target gas component is $H_2S$. The line "II" means that the target gas component is $CH_3SH$. The line "III" means that the target gas component is $(CH_3)_2S$.

Figure 6:
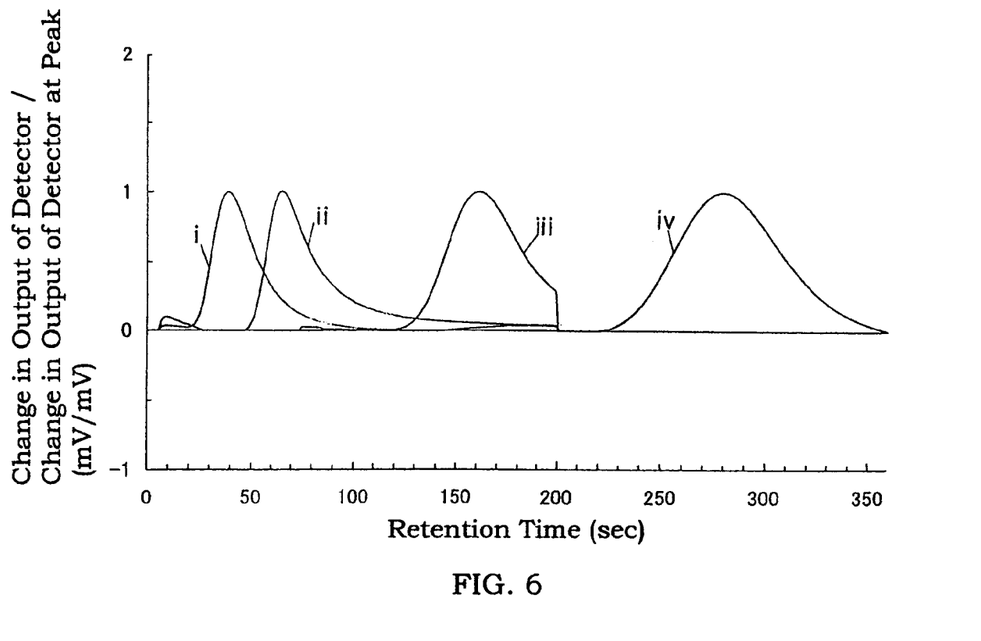
FIG. 6 shows normalized curves registered in the processor unit of the gas chromatograph.

In addition, the peak curve (i) of FIG. 6 corresponds to a constant component (i.e., the background component in breath) such as $CO_2$ or $O_2$ included in human breath. The peak curve (ii) corresponds to $H_2S$. The peak curve (iii) corresponds to $CH_3SH$. The peak curve (iv) corresponds to $(CH_3)_2S$. The time corresponding to the respective peak is the retention time.

Therefore, the processor unit 33 can measure a length of time that elapses before the peak appears according to the output of the detector 30 for detecting the gas provided from the gas separation column 1 and the gas injection timing detected. By comparing the thus measured retention time of the target gas component and the waveform of the detected peak with the data registered in the memory 33a, the target gas component is decided. In addition, the concentration (quantitative value) of the target gas component can be decided from the peak value of the detected output. The decision results are indicated on the display 34.

Figure 7:
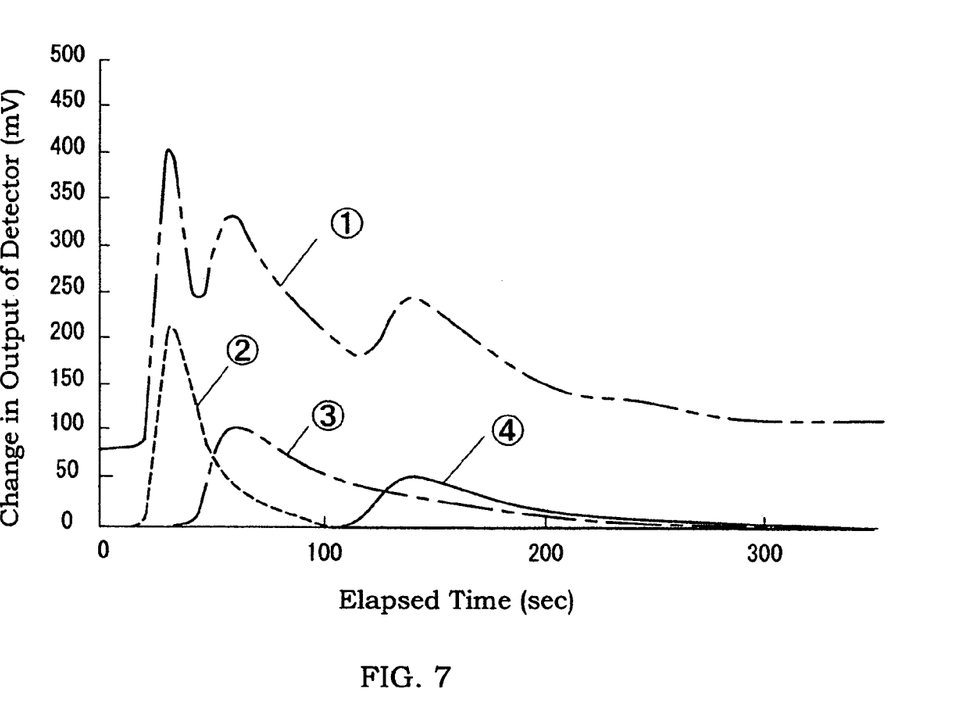
FIG. 7 is a chromatograph obtained by a breath component analyzer using the gas chromatograph.

FIG. 7 shows a gas chromatogram obtained using the gas chromatograph 6 of this embodiment with respect to gas components corresponding to breath odor in a breath gas. In FIG. 7, ① shows measured data, ② is a separated curve showing the background of the breath gas, ③ is a separated curve of $H_2S$, and ④ is a separated curve of $CH_3SH$. There is no $(CH_3)_2S$ in the measured data.

Figure 8:
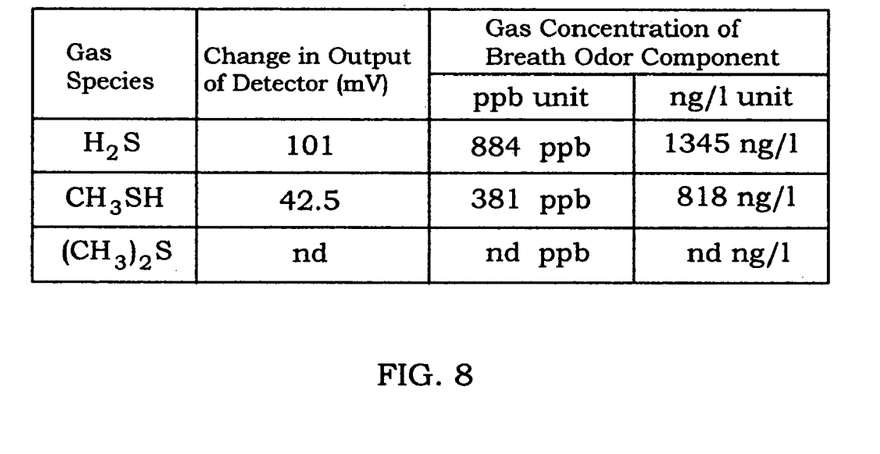
FIG. 8 shows analysis results indicated on a display of the breath component analyzer.

For example, the measurement results are indicated on the display 34, as shown in FIG. 8. In this example, gas species, change (mV) in output of the detector 30, and gas concentration of breath odor component are displayed. For the conversion into the gas concentration, the concentration may be calculated from the area of peak waveform in place of using the peak height of the detected output.

By the way, when a change in flow amount of the carrier gas occurs for some reason, the retention time is fluctuated, so that the analysis accuracy may deteriorate. In this case, according to the fact that the gas component providing the initial peak of the detected output by the detector 30 is the constant component such as $CO_2$ or $O_2$ essentially included in human breath, a displacement between a standard retention time of this constant component and the retention time corresponding to the peak that appears later of the detected output can be calculated by the processor unit 33. By correcting the retention time of $H_2S$, $CH_3SH$, or $(CH_3)_2S$ described above according to the calculation results, the influence of the flow fluctuation of the carrier gas can be eliminated.

Figure 9:
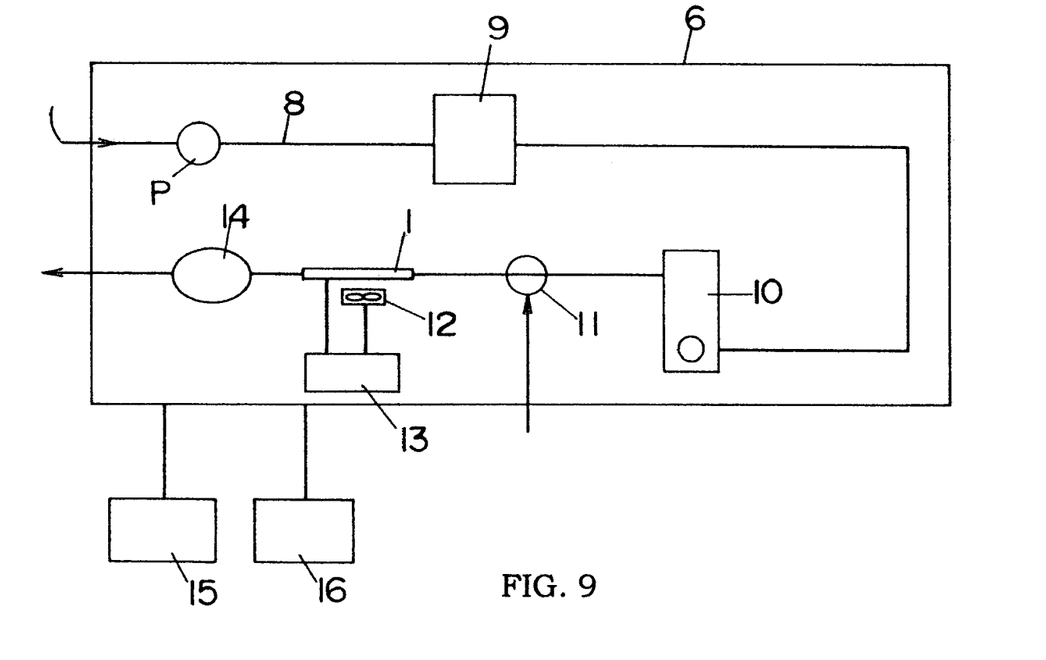
FIG. 9 is a schematic diagram illustrating a flow channel configuration of a gas chromatograph having no buffer tank.

Inconveniences may be caused when the air (i.e., outside air) is supplied to the gas separation column 1 by the air pump P without the formation of the buffer tank. For reference, they are explained below.

Figure 10A:
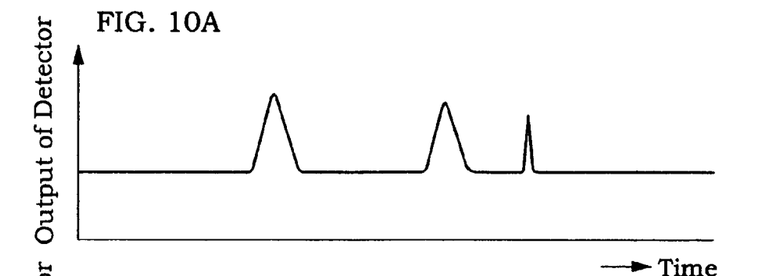
FIGS. 10A to 10C are graphs explaining inconveniences that may be caused by use of the device of FIG. 9.
Figure 10B:
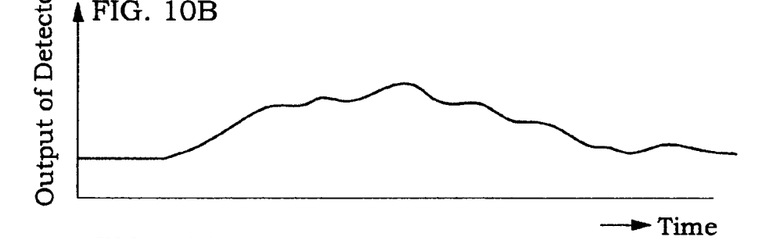
Figure 10C:
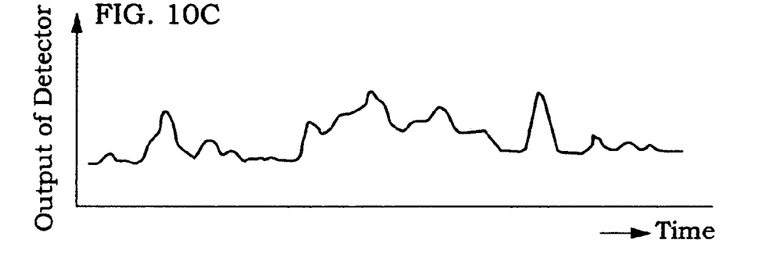

That is, as shown in FIG. 9, this gas chromatograph is characterized in that the air pump P is provided upstream of the flow regulator 9, one end of the gas flow channel 8 is communicated with outside without the formation of the buffer tank, and the air is sent to the gas separation column 1 through the gas flow channel 8 by the air pump P. When a miscellaneous gas is mixed in the air supplied by the air pump for a short time period, there is a fear that output levels appear in separate parts on the baseline of output of a detector 14, as shown in FIG. 10A. In addition, when the miscellaneous gas is mixed in the air supplied by the air pump for a relatively long time period, there is a fear that the baseline becomes higher over a long time period, as shown in FIG. 10B. Moreover, when a contaminated air is supplied by the air pump, a fluctuation of the baseline may occur, as shown in FIG. 10C.

Second Embodiment

Figure 11:
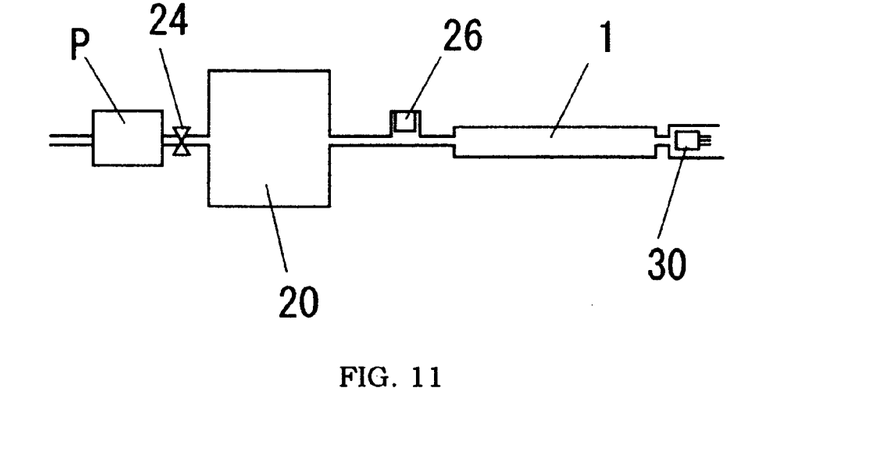
FIG. 11 is a schematic diagram illustrating a flow channel configuration of a gas chromatograph according to a second embodiment of the present invention.

As described above, the first embodiment is characterized in that the buffer tank 20 is disposed upstream of the air pump P, and a part of the air (excessive air) supplied from the pump is returned to the buffer tank 20. However, in the present embodiment, as shown in FIG. 11, a buffer tank 20 is formed in a gas flow channel between a flow regulator 24 and a gas injection port 26. That is, the air sucked by an air pump P is flow controlled by the flow regulator 24, and then sent as the carrier gas to a gas separation column 1 through the buffer tank 20. When the air pump P has a large suction capacity, the excessive air may be discharged outside. Other configurations are substantially the same as the first embodiment. Therefore, duplicate explanations are omitted.

Third Embodiment

The retention time described above depends on the flow amount of the carrier gas. Therefore, as the flow amount of the carrier gas increases, the retention time becomes earlier (shorter). In addition, there is a case that it takes a very long time (slow) to come out from the gas separation column 1 with respect to a specific gas component. In such a case, there is a fear that the detection time is extended, and the conversion of concentration becomes inaccurate because the detector output is provided by a broad peak.

Figure 12:
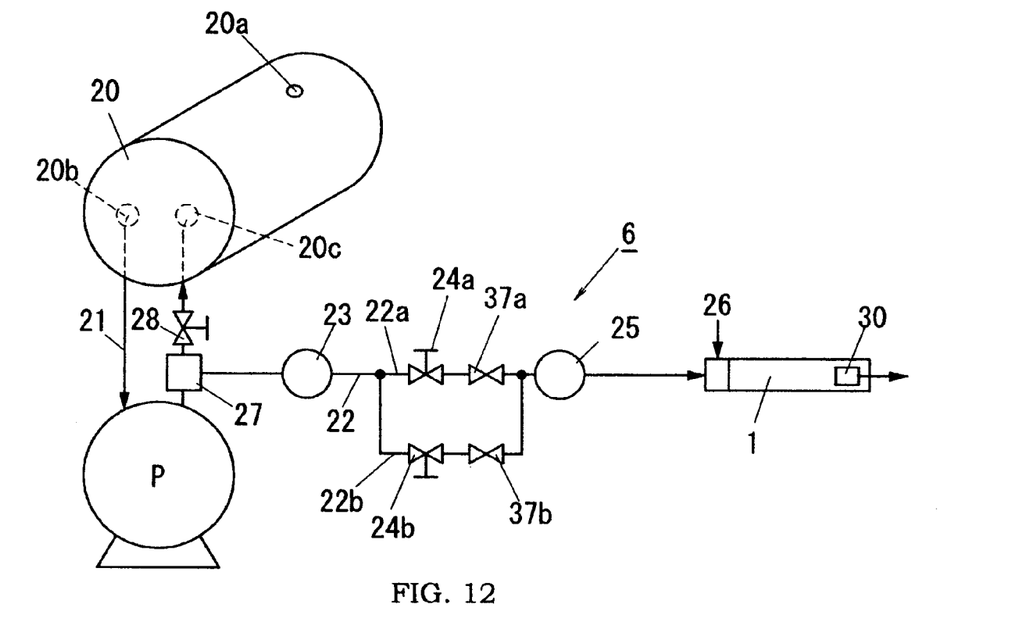
FIG. 12 is a schematic diagram illustrating a flow channel configuration of a gas chromatograph according to a third embodiment of the present invention.

Therefore, the gas chromatograph of the present embodiment is characterized by shortening the detection time of the gas component having a long retention time, and performing a control such that the flow amount of the carrier gas is increased according to a required pattern from the time of detecting gas injection to make the peak of the detector output sharp.

FIG. 12 is a schematic diagram showing a flow channel configuration of this gas chromatograph. A gas flow channel 22 comprises a first gas flow channel 22a having a flow regulator 24a for controlling a flow amount and an electromagnetic valve 37a, and a second gas flow channel 22b provided in parallel with the first gas flow channel, and having a flow regulator 24b for controlling the flow amount and an electromagnetic valve 37b.

The first gas flow channel 22a is used to flow a required amount of the carrier gas before the injection of the subject gas. The second flow channel 22b is used to increase the flow amount of the carrier gas after the injection of the subject gas. Each of the flow regulators 24a, 24b is previously adjusted to provide the required flow amount. In ordinary practice, a control is performed by the processor unit 33 such that the electromagnetic valve 37a is opened, and the electromagnetic valve 37b is closed. On the other hand, when the injection of the subject gas is detected, the flow amount of the carrier gas is controlled by opening the electromagnetic valves 37a, 37b according to a flow change pattern previously registered in the memory 33a. The first and second gas flow channels 22a, 22b may be disposed in the gas intake channel 21 extending between the buffer tank 20 and the air pump P.

It is also preferred that the an amount of the air sucked from the outside is increased by controlling the voltage applied to the air pump P, and the flow regulator is replaced by an electrically controllable needle valve. For example, when the voltage applied to the air pump P is controlled by an inverter, it is possible to gradually increase the flow amount of the carrier gas. Other configurations are substantially the same as the first and second embodiments. Therefore duplicate explanations are omitted.

Fourth Embodiment

Figure 13:
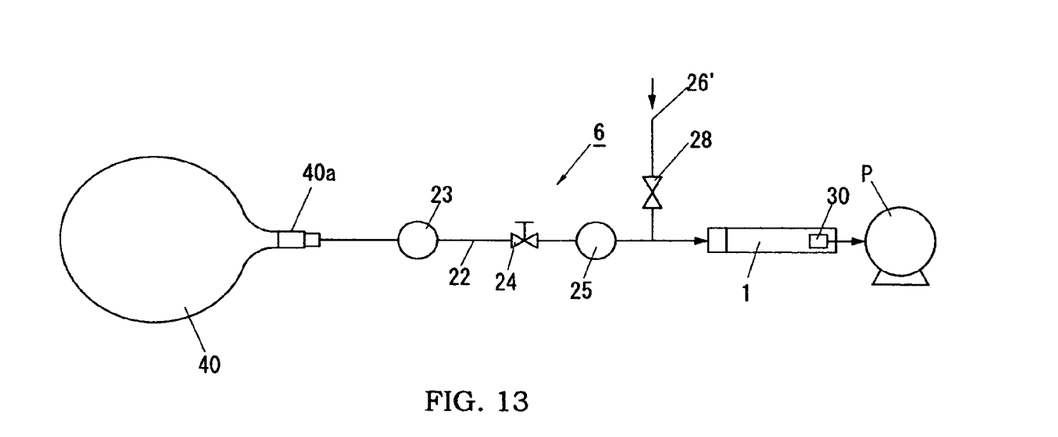
FIG. 13 is a schematic diagram illustrating a flow channel configuration of a gas chromatograph according to a fourth embodiment of the present invention.

In the first to third embodiments described above, it is essential to use the buffer tank 20. As shown in FIG. 13, the gas chromatograph of this embodiment is characterized by using a bag-type tank 40 having a variable volume such as a rubberized bag in place of the buffer tank 20.

That is, a clean air for the carrier gas is previously charged in this bag-type tank 40. A connection port 40a formed at an outlet of the bag-type tank 40 is connected to an end of a gas flow channel 22. The air of the bag-type tank 40 is sucked in a gas separation column 1 together with a subject gas by an air suction pump P disposed at the discharge side of the gas separation column 1.

This analyzer can be also used in the case that the subject gas is air. A gas supply port (hereinafter referred to as a gas suction port) 26' is connected to the gas flow channel 22 through an electromagnetic valve 28. In the case of detecting a gas component included in the air, the gas suction port 26' is opened to outside, and the air of the subject gas is sucked in the gas flow channel 22 kept in a negative pressure state by operating a manual switch to open the electromagnetic valve 28.

The air sucked in the gas flow channel 22 is sent to the gas separation column 1 together with the carrier gas. The connection port 40a of the bag-type tank 40 is closed when it is not connected to the gas flow channel 22. Therefore, there is no leakage of the air from the bag-type tank 40. When the connection port is connected to the gas flow channel 22, it can be opened through a valve structure. When the gas chromatograph 6 is not used, the bag-type tank 40 can be detached.

The present embodiment explains about the case of detecting the gas component included in the air. However, when using the gas chromatograph 6 as the breath component analyzer, a subject-gas (breath gas) bag accommodating the subject gas therein may be connected to the gas suction port 26'. Other configurations are substantially the same as the first to third embodiments. Therefore, duplicate explanations are omitted.

Each of the gas chromatographs 6 of the above embodiments can be used to an analyzer for another subject gas as well as the breath component analyzer. Therefore, the present invention is not limited to the above embodiments.

INDUSTRIAL APPLICABILITY

As described above, according to the present invention, even when a miscellaneous gas component is included in the carrier gas of the air sucked by the air pump, the flow of the air is weakened by the buffer tank to make the concentration of the miscellaneous gas component uniform, and then sent to the gas separation column. Therefore, it is possible to prevent a baseline fluctuation of output of the detector caused by the presence of the miscellaneous gas component, and provide a reliable measurement by minimizing the influence of the baseline fluctuation on the componential analysis. In addition, even if the flow amount of the carrier gas increases, or the gas component slowly comes out from the gas separation column, it is possible to shorten a detection time of the gas component having a slow retention time by performing a control of increasing the flow amount of the carrier gas according to a required pattern from the time of detecting the gas injection, and obtain a sharp peak of the detector output.

In addition, as described above, the gas chromatograph of the present invention is particularly suitable to the breath component analyzer. However, it can be widely utilized in qualitative/quantitative analysis of another subject gas because the baseline of output of the detector is stabilized to provide reliable measurement.

The invention claimed is:

1. A gas chromatograph comprising:
   a gas separation column accommodating a member for causing a flow delay depending on gas component;
   an air pump for supplying an air as a carrier gas into said gas separation column;
   a gas supply port formed in a gas flow channel extending between said air pump and said gas separation column, and adapted to supply a subject gas containing a target gas component to be detected into the air flowing in said gas flow channel;
   a buffer tank provided upstream of said gas supply port, and having the capability of retaining a larger amount of the air than the amount of the air supplied per unit of time into said gas separation column by said air pump; and
   a detector for detecting the gas component of said subject gas supplied to said gas separation column,
   wherein said buffer tank has a suction port opened to outside, and a discharge port connected to said air pump so that the air sucked by said air pump through said buffer tank is sent to said gas separation column through said gas flow channel.

2. The gas chromatograph as set forth in claim 1 further comprising a sensor for sensing a timing of injecting said subject gas into said gas flow channel, and analysis means for analyzing said subject gas according to the timing provided from said sensor and an output of said detector.

3. The gas chromatograph as set forth in claim 1, wherein a part of the air supplied to said gas flow channel by said air pump is sent to said gas separation column, and the rest of the air is returned from said gas flow channel to said buffer tank through a branch channel.

4. The gas chromatograph as set forth in claim 1 further comprising a gas purifier using at least one of a gas decomposition catalyst and a gas absorption material, which is disposed upstream of said gas supply port in said gas flow channel.

5. The gas chromatograph as set forth in claim 1, further comprising a flow sensor disposed upstream of said gas supply port and at the vicinity of said gas supply port in said gas flow channel, and means for detecting a supply of said subject gas according to a change in output of said flow sensor.

6. The gas chromatograph as set forth in claim 1 further comprising a flow sensor disposed downstream of said detector and at the vicinity of said detector in said gas flow channel, and means for detecting a supply of said subject gas according to a change in output of said flow sensor.

7. The gas chromatograph as set forth in claim 1, further comprising a controller for increasing a flow amount of said carrier gas supplied into said gas separation column according to a predetermined pattern from the time point of supplying said subject gas.

8. A breath component analyzer comprising:
   the gas chromatograph as set forth in claim 1;
   a memory for storing reference data including a retention time previously determined by the gas chromatograph with respect to a breath odor sample having a known gas component; and
   analysis means for comparing measurement data including a retention time determined by the gas chromatograph with respect to a breath odor to be measured with the reference data.

9. The breath component analyzer as set forth in claim 8 comprising means of correcting a fluctuation amount of the retention time of the gas component corresponding to the breath odor to be detected according to the fluctuation amount of the retention time of a constant component in breath.

10. The gas chromatograph as set forth in claim 1, wherein said gas separation column comprises an external cylinder made of a metal having high thermal conductivity, and a heater wound around an outer peripheral surface of said external cylinder.

11. The gas chromatograph as set forth in claim 1, wherein said gas separation column comprises a double cylinder composed of an external cylinder made of a metal having high thermal conductivity, and an internal cylinder inserted in said external cylinder, a filling material filled as a stationary phase in said internal cylinder, and a heater disposed on said external cylinder.

12. The gas chromatograph as set forth in claim 11, wherein said heater is wound in a spiral manner around an outer peripheral surface of said external cylinder from its one end toward the opposite end.

* * * * *

UNITED STATES PATENT AND TRADEMARK OFFICE
CERTIFICATE OF CORRECTION

PATENT NO. : 7,194,890 B2  Page 1 of 1
APPLICATION NO. : 10/506421
DATED : March 27, 2007
INVENTOR(S) : Katsuyuki Tanaka et al.

It is certified that error appears in the above-identified patent and that said Letters Patent is hereby corrected as shown below:

Title Page:
Item (54) should be read as follows:
-- GAS CHROMATOGRAPH, AND BREATH COMPONENT ANALYZER USING THE SAME --.

Signed and Sealed this

Twenty-sixth Day of June, 2007

JON W. DUDAS
*Director of the United States Patent and Trademark Office*